United States Patent
Kreidler

(10) Patent No.: US 9,247,937 B2
(45) Date of Patent: Feb. 2, 2016

(54) NEEDLE ATTACHMENT FOR A SURGICAL SEWING INSTRUMENT

(75) Inventor: Bodo Kreidler, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 905 days.

(21) Appl. No.: 12/256,714

(22) Filed: Oct. 23, 2008

(65) Prior Publication Data

US 2009/0112258 A1    Apr. 30, 2009

(30) Foreign Application Priority Data

Oct. 25, 2007   (DE) .......................... 10 2007 052 185

(51) Int. Cl.
   *A61B 17/06*    (2006.01)
   *A61B 17/00*    (2006.01)

(52) U.S. Cl.
   CPC ..... *A61B 17/06066* (2013.01); *A61B 17/06109* (2013.01); *A61B 2017/00477* (2013.01); *A61B 2017/0608* (2013.01); *A61B 2017/06052* (2013.01)

(58) Field of Classification Search
   CPC ................... A61B 17/06066; A61B 17/06109; A61B 2017/00477; A61B 2017/06052; A61B 2017/0608; A61B 17/0401; A61B 17/0469
   USPC ......... 606/222, 223, 224, 225, 226, 227, 167, 606/232, 147
   See application file for complete search history.

(56) References Cited

U.S. PATENT DOCUMENTS

| 2,830,587 | A | * | 4/1958 | Everett .......................... 604/272 |
| 3,840,017 | A | * | 10/1974 | Violante ....................... 606/146 |
| 4,103,690 | A |   | 8/1978 | Harris |
| 4,741,330 | A | * | 5/1988 | Hayhurst ...................... 606/144 |
| 5,330,468 | A |   | 7/1994 | Burkhart |
| 5,769,862 | A |   | 6/1998 | Kammerer et al. |
| 6,168,611 | B1 | * | 1/2001 | Rizvi .............................. 606/222 |
| 6,309,401 | B1 | * | 10/2001 | Redko et al. ................... 606/185 |
| 6,629,984 | B1 | * | 10/2003 | Chan .............................. 606/148 |
| 2004/0210245 | A1 | * | 10/2004 | Erickson et al. ............... 606/167 |
| 2005/0033365 | A1 |   | 2/2005 | Courage |
| 2006/0229642 | A1 |   | 10/2006 | Oberlaender et al. |

FOREIGN PATENT DOCUMENTS

DE   102004024188 A1   2/2006
DE   10 2005 015 687 A1   10/2006

OTHER PUBLICATIONS

"Arthroscopy, Sports Medicine, Spinal Surgery", 2nd edition Jan. 2005, p. 106 (Bulletin ART-SHF 14A) by Karl Storz Gmbh & Co. KG, Tuttlingen Germany.
European Search Report; Application No. EP 08 16 7424; Feb. 11, 2009; 5 pages.

* cited by examiner

*Primary Examiner* — Gregory Anderson
*Assistant Examiner* — Christina Lauer
(74) *Attorney, Agent, or Firm* — Whitmyer IP Group LLC

(57) ABSTRACT

A needle attachment for a surgical sewing instrument has a proximal-side connector for connecting to a sewing instrument. The needle attachment has a hollow shaft-like body which has a curved hollow needle on the distal side. A thread can be guided through the needle attachment. The cross-section of the curved hollow needle is oval.

11 Claims, 3 Drawing Sheets

NEEDLE ATTACHMENT FOR A SURGICAL SEWING INSTRUMENT

BACKGROUND OF THE INVENTION

The invention relates to a needle attachment for a surgical sewing instrument with a proximal-side connector for connecting to a sewing instrument, with a hollow shaft-like body, which has a curved hollow needle on the distal side, whereby a thread or a thread bundle can be guided through the needle attachment.

The invention further relates to a surgical sewing instrument having attached such a needle attachment.

Such a needle attachment and such a surgical sewing instrument to be connected with the needle attachment is known from the catalog "Arthroscopy, Sports Medicine, Spinal Surgery", 2nd edition January 2005, page 106 (Bulletin ART-SHF 14A) by Karl Storz GmbH & Co. KG, Tuttlingen, Germany. This surgical sewing instrument has an approximately rod-like body, through which a surgical thread is guided from proximal to distal to a distal suture attachment. A recess, along which a section of the thread is guided exposed, is left open in the body of the sewing instrument.

This surgical sewing instrument can be connected to various needle attachments, distinguished in particular by variously bent and formed curved hollow needles.

For this the needle attachment has a hollow shaft-like body which proximally has a connector for connecting to the surgical sewing instrument. The surgical thread or the thread bundle guided in through the body of the surgical sewing instrument is also guided in through a needle attachment and exits at a tip of the curved hollow needle. In the case of surgical threads which are designed as relatively stiff, but yet flexible bodies it is no problem to push the thread through the curved or sometimes even volute hollow needle until it exits at the distal end in the region of the tip of the hollow needle. The thread must however exhibit a certain stiffness in a longitudinal direction so that it can be pushed through the relatively long stretch of the needle attachment, approximately 150 mm. For this, it was established to equip the lumen of the hollow needle with a circular cross-section, which corresponds approximately to the cross-section of the thread.

In a further development of the sewing technology with sewing materials in particular which are inclined to splice, the distal end of the thread or thread bundle was provided with a relatively stiff end section, for example by a sleeve being pressed onto this end or the end region being stuck. With many sewing techniques the thread should not comprise monofilament, rather multifilament, where the ends of the multifilaments must be connected or stuck together by such a stiff sleeve for handling purposes.

With curved needles, in particular in highly curved needles, it is now no longer possible to push the stiff end sections, where required measuring several centimetres, through a hollow body, whereof the lumen corresponds approximately to the outer diameter. The stiffened end section would become jammed in such a curve or become wedged and could no longer be distally pushed.

Relatively large-lumen hollow needles must be provided to make sufficient space available for the stiff end section, so that these can move round the curve. This results in a relatively thick needle which causes a large-size puncture site in the tissue to perform the sewing procedure.

But this is in contrast to the general aim in surgery of carrying out such a procedure with the least possible trauma.

It is therefore an object of the present invention to provide a remedy in this case and develop a needle attachment to the extent where it also enables threads to be pushed through with a stiffened thread end, with the smallest possible structure.

SUMMARY OF THE INVENTION

According to one aspect of the invention this object is achieved by a needle attachment for a surgical instrument, comprising a hollow shaft-like body, a connector on a proximal end of said hollow shaft-like body for connecting said needle attachment to a surgical element, a curved hollow needle at a distal end of said hollow shaft-like body, wherein a cross section of said curved hollow needle is oval, said cross section being taken perpendicular to a longitudinal center axis of said curved hollow needle.

This object is further achieved by a surgical sewing instrument with an approximately rod-like body, through which a surgical thread or a thread bundle can be guided from proximal to distal, wherein the rod-like body is connected to a needle attachment having a hollow shaft-like body, a connector on a proximal end of said hollow shaft-like body connected to the distal end of the surgical sewing instrument, a curved hollow needle at the distal end of the hollow shaft-like body of the needle attachment, wherein the cross section of said curved hollow needle is oval, said cross section is taken perpendicular to a longitudinal center axis of the curved hollow needle.

An advantage of this measure is that the longer axis of the oval allows the stiffened thread end to move round a curve without this stiff section being wedged or jammed. Since this space is needed in one plane only, specifically in the plane of the curve, it suffices if the lumen is enlarged or respectively stretched in this direction only, specifically along the longer diameter of the oval. In the transverse direction, that is to say along the shorter axis of the oval, this space is not needed, so that the lumen does not have to be widened in this direction.

It is also a considerable advantage of this measure that the resulting cross-sectional volume is substantially less than the cross-sectional volume of a hollow needle with circular cross-section, whereof the diameter corresponds to the longer axis of the oval cross-section. The term cross-sectional volume concerns the space necessary to penetrate the curved needle into a tissue. This also reduces the puncture volume, meaning that this procedure can be carried out with substantially less trauma than with a needle having a round cross-section and the diameter of the long axis of the oval.

At the same time the oval configuration allows the hollow body of the needle to be formed with a lesser wall thickness, since the geometry of the oval permits greater forces to be absorbed, which act in the direction of the longer axis, than in a circular body. Since, when a curved needle punctures tissue, resistance forces act in particular on the curved area, the oval geometry permits greater forces to be absorbed, resulting in hollow needles with thinner wall thicknesses, if these have an oval cross-section.

In another configuration of the invention the longer axis of the oval cross-section extends in the bending plane of the curved hollow needle.

As mentioned earlier, space is required substantially in this plane to push through the stiffened end section of the thread. With this alignment of the oval the end of the thread, without its having to skew or twist or deviate from this plane, can be pushed through easily and thus with minimal resistance through the curved area of the needle.

In another configuration of the invention the short axis of the oval cross-section corresponds approximately to the diameter of the stiffened distal end of the thread or of the thread bundle.

The advantage of this measure is that the stiffened end section is guided laterally in this direction such that no wedging of this section can occur when the curved hollow needle is traversed, but this procedure can run purposefully guided by this lateral guiding.

In another configuration of the invention the cross-section is designed as a flat oval.

The considerable advantage of this measure is that the opposite straight walls of the flat oval can absorb very strong compressive or tensile forces. As mentioned earlier, during the puncturing procedure relatively strong forces act on the curved hollow needle, which itself represents an extremely slender body with a diameter in the region of 1 to 2 mm. Forces, which might cause widening or straightening of the curve, act through the resistance forces during puncturing tissue. These forces can now be properly absorbed by the flat oval sides such that the wall thickness can be selected even less than for a needle with circular cross-section as a result.

It is understood that the abovementioned features and those yet to be explained hereinbelow can be used not only in the respectively specified combinations, but also in other combinations or individually, without departing from the scope of the present invention.

BRIEF DESCRIPTION OF THE DRAWINGS

The invention will be described and explained in greater detail hereinbelow by means of a selected exemplary embodiment in connection with the attached diagrams, in which:

FIG. 6 shows a longitudinal section comparable to the illustration of FIG. 2 of the distal end region of a needle attachment, wherein a thread with a stiffened distal thread end is pushed in.

DETAILED DESCRIPTION OF A PREFERRED EMBODIMENT

Figure 1:
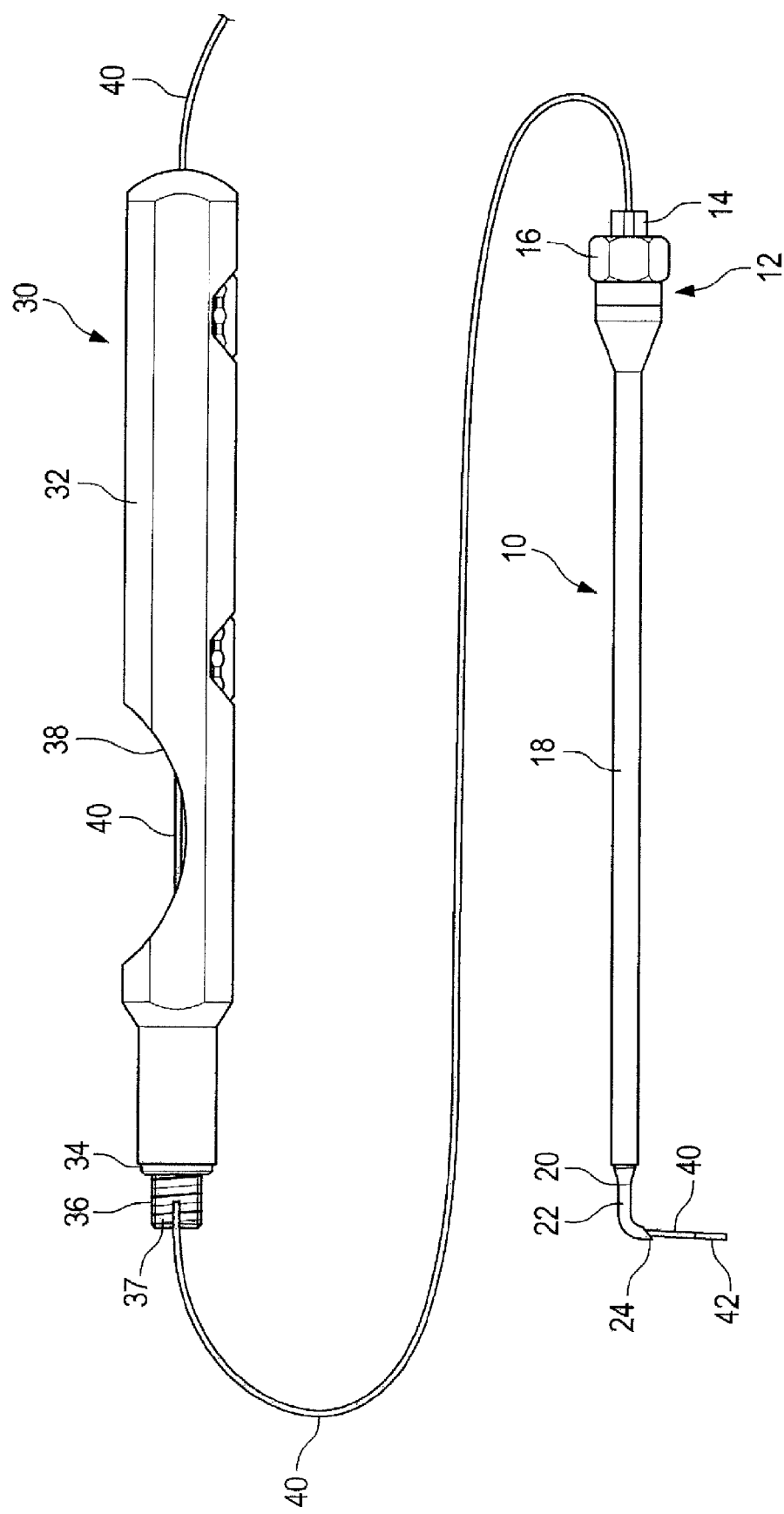
FIG. 1 shows an exploded view of a surgical sewing instrument which can be connected to a needle attachment, illustrating how a surgical thread is guided both through the surgical sewing instrument and also through the needle attachment.

A needle attachment for a surgical sewing instrument illustrated in a figure is designated in its entirety by reference numeral 10.

As is evident in particular from FIG. 1, the needle attachment 10 has on a proximal side a connector 12. The connector 12 has a proximally projecting journal 14 which is enclosed by a retainer nut 16. A thin hollow shaft-like body 18 with an outer diameter of approximately 2 mm and a length of for example 150 mm extends from the connector 12. At a distal end 20 the body 18 merges into a curved hollow needle 22 which terminates in a angled tip 24, as is standard for needles or syringes which are to puncture tissue.

The needle attachment 10 is provided to be connected to a surgical sewing instrument, designated in FIG. 1 in its entirety by reference numeral 30.

The surgical sewing instrument 30 has an approximately rod-like body 32 configured as a handgrip. At a distal end 34 a connector 36 protrudes which is configured such that the journal 14 can be pushed into it on the proximal end of the needle attachment 10. A fixed screw connection can then be created with the outer thread 37 of the connector 36 via the retainer nut 16, fitted with an inner thread.

This connection can however also be designed differently, for example as a bayonet connection, as a snap-in connection or also as a permanent fixed connection, if the surgical sewing instrument 30 is to be used with only a single needle attachment having a quite specifically configured hollow needle. Usually, however, the surgical sewing instrument 30 is available with a whole set of various needle attachments, as is evident from the catalog of the applicant mentioned at the outset.

A surgical thread 40 can be threaded through the rod-like body 32 of the surgical sewing instrument 30 from proximal to distal, whereby a section of the thread is exposed in the region of recess 38 in the rod-like body 32. An operation holding the rod-like body 32 manually can move the thread 40 reciprocally, for example with a thumb gripping into the recess 38. The thread 40 can be a single thread or composed of a bundle of threads.

The thread 40 is inserted via the hollow journal 14 of the connector 12 of the needle attachment 10 into the interior of the body 18, fed through the latter and exiting at the tip 24 of the curved hollow needle 22, as illustrated in FIG. 1.

FIG. 1 also shows that the thread 40 has a stiffened distal end 42.

Figure 4:
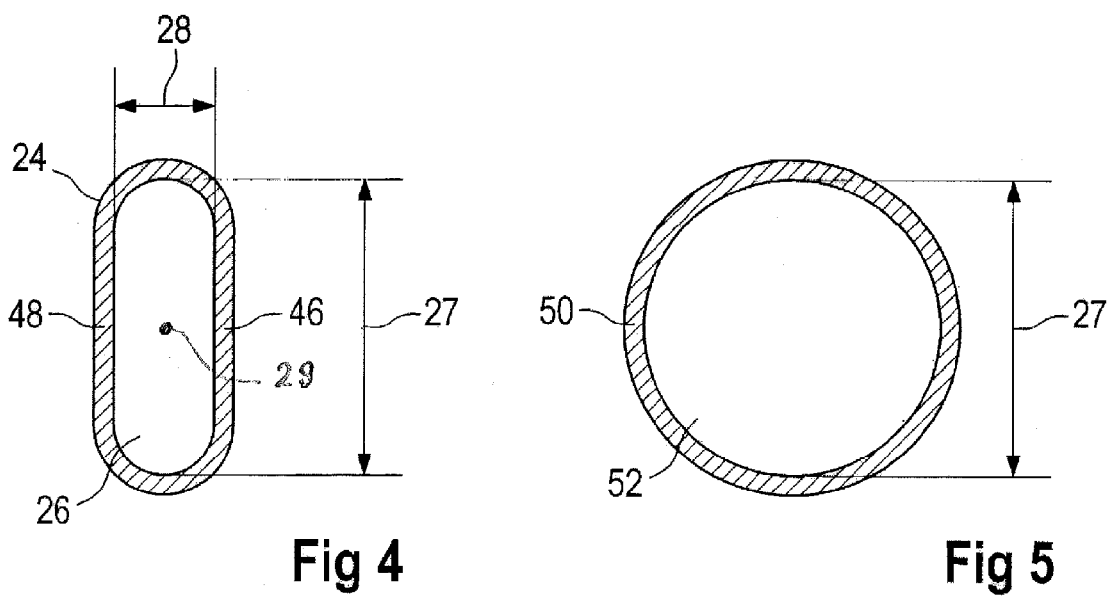
FIG. 4 shows a cross-section along line IV-IV in FIG. 2.

The cross-section 26 of the hollow needle 22 is oval in order for this stiffened end 42 to be guided round the curve of the curved hollow needle 22, as is evident in particular from FIG. 4. The cross-section is always taken perpendicular to a longitudinal center axis 29 of the hollow needle 27. Any cross-section taken perpendicular along the center axis 29 is oval. The oval is designed as a flat oval, that is, both opposite sides 46 and 48 are flat or respectively run straight, as is evident, and in each case merge into one another via semicircular curves.

The oval cross-section 26 has a longer axis 27 and a shorter axis 28. The length ratio illustrated here is approximately 3:1.

Figure 2:
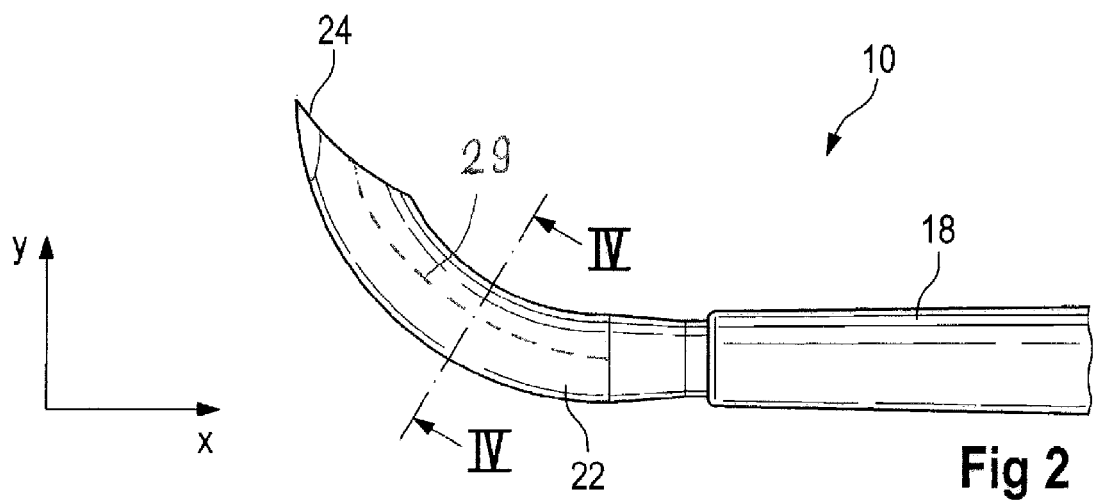
FIG. 2 shows a greatly enlarged selective side elevation of the distal end region of the needle attachment with the curved hollow needle.
Figure 3:
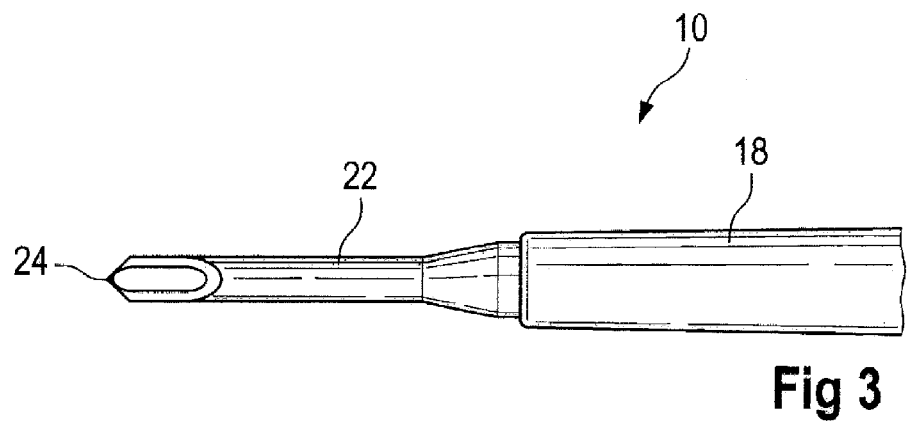
FIG. 3 shows a plan view turned through 90° of the longitudinal axis of the region of FIG. 2.

The alignment of the longer axis 27 is such that it extends in the plane of the curve of the hollow needle 22, as illustrated in FIG. 2 by the plane coordinates x and y. The plan view of FIG. 3 shows that the curved hollow needle 22 is configured more narrowly here than in the side elevation evident in FIG. 2.

Figure 7:
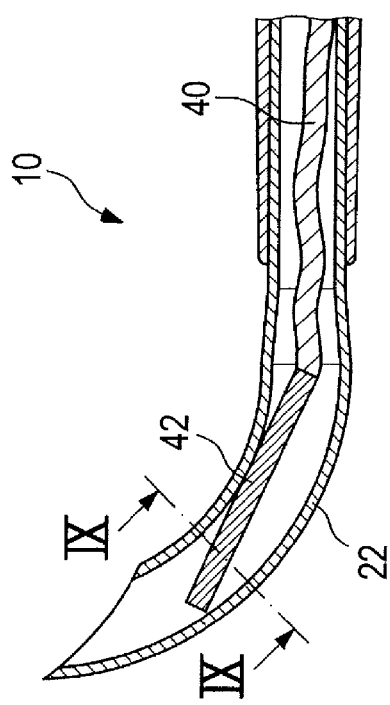
FIG. 7 shows an illustration comparable to the illustration of FIG. 6, wherein the stiffened thread end is pushed further in to the curved area.
Figure 6:
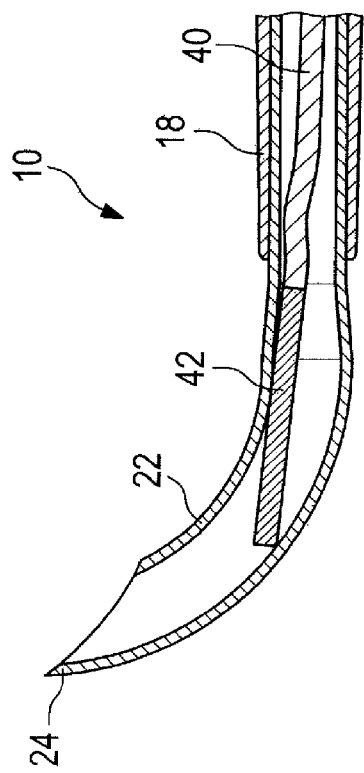
Figure 8:
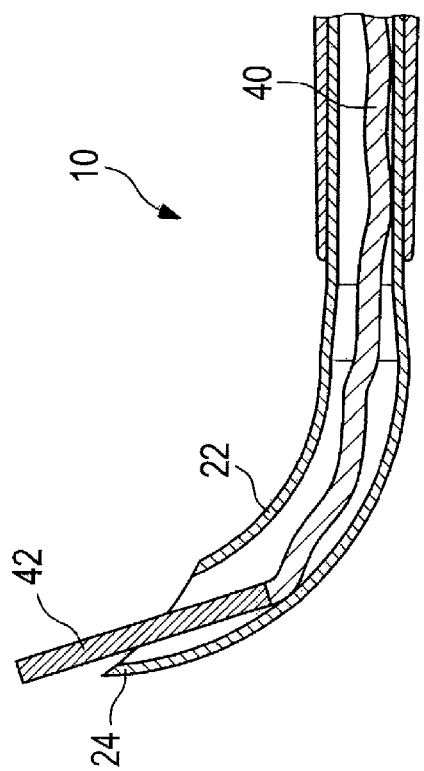
FIG. 8 shows an illustration comparable to the illustration of FIGS. 6 and 7, wherein the stiffened thread end is just being pushed out of the tip of the needle.

The particular advantage of the invention will now be described by way of the sequence of figures from FIG. 6 to 8.

As already mentioned, the thread 40 has stiffened end section 42. This stiffened end is to be threaded trouble-free through the rod-like body 32 of the sewing instrument 30 extending in a straight line and through the hollow shaft-like body 18 of the needle attachment 10 extending in a straight line. Due to the configuration of the oval cross-section 26 (see FIG. 4) the stiffened section 42 in the region of the curved hollow needle 22 now has sufficient space available to run through the curved area, as is evident from the sequence of figures from FIG. 6 to FIG. 7 to FIG. 8. It is obvious that the stiffened section 42 can be pushed kink-free and wedge-free through the curve of the hollow needle 22.

Figure 9:
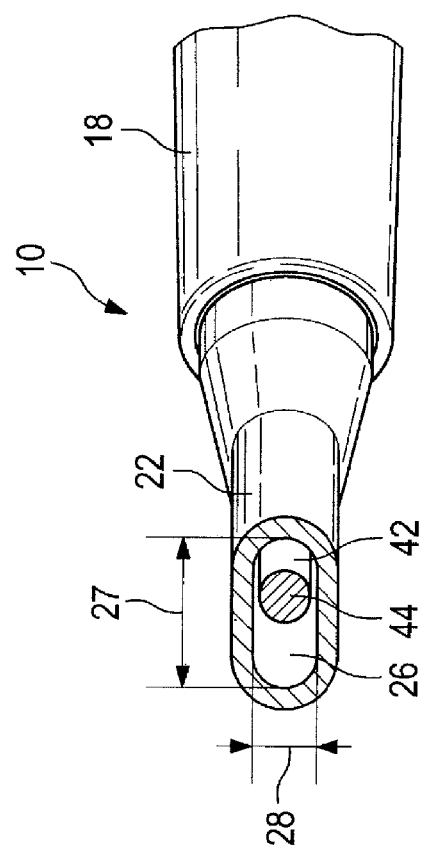
FIG. 9 shows a section along line IX-IX in FIG. 7.

It is evident from the cross-sectional view of FIG. 9 that the dimension of the shorter axis 28 of the oval cross-section 26 corresponds approximately to the outer diameter 44 of the stiffened end 42.

The length dimension of the longer axis 27 and the radius of curvature of the curve determine the length dimension of the stiffened end 42 which can be pushed through or accordingly vice versa, depending on which condition must be taken into consideration. It is also evident from the cross-sectional view of FIG. 9 that the stiffened thread end 42 is guided sideways through both flat sides 46 and 48 of the flat oval in a lateral direction, that is to say extending along the shorter axis 28, excluding deviation or tilting in this direction.

Figure 5:
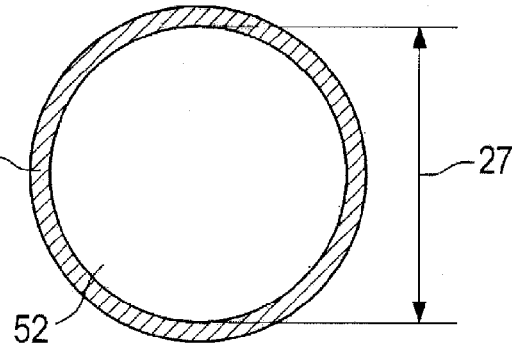
FIG. 5 shows a cross-section of a hollow needle with circular cross-section comparable to the longer axis of the oval of FIG. 4.

A further advantage of the invention can be gained from comparing FIG. 4 and FIG. 5. As described earlier, the dimension of the longer axis 27 of the oval cross-section 26 in conjunction with the flat sides 46, 48 initiates the properly guided, wedge-free motion of the stiffened end 42 through the curved hollow needle. FIG. 5 illustrates a hollow needle of circular cross-section, the inner diameter of which corresponds to the dimension of the longer axis 27.

The stiffened end 42 could likewise be pushed through such a curved hollow needle, only the hollow needle body or respectively the volume of the hollow needle body would be substantially bigger, resulting in a substantially larger puncture site in the tissue.

Neither could it be discounted for the stiffened end section 42 to be wedged to the side and possibly be jammed, as it could also dodge sideways, though this is prevented by the configuration, as evident in particular in FIG. 9.

Here therefore not only is less space needed for puncturing the tissue with the hollow needle 22 to be performed with less trauma, but also guiding through the stiffened thread end 42 can be done substantially more securely.

A further advantage can also be gained from comparing FIG. 4 and FIG. 5, specifically that the flat sides 46 and 48 can absorb substantially greater deformation forces than the body shown in FIG. 5 by being formed as a flat oval. These forces will act as resistance forces during puncturing to the extent where the curve widens slightly, that is, these forces act substantially in the direction of the longer axis 27.

Since these forces can be absorbed substantially better due to geometry, this offers the possibility of reducing the wall thickness of the flat oval.

The abovementioned exemplary embodiment illustrated a thread in the form of a monofilament which has a stiffened end 42.

The invention also has a particularly favourable effect with multifilament threads, whereof the distal ends are combined together by a sleeve or a correspondingly stuck-together end. Such an assembly can likewise easily be moved in through the curved hollow needle 22.

What is claimed is:

1. A needle attachment assembly for a surgical instrument, comprising:
   a hollow shaft-like body,
   a connector on a proximal end of said hollow shaft-like body for connecting the needle attachment to a surgical instrument,
   a curved hollow needle at a distal end of said hollow shaft-like body the curved hollow needle having a cross-section configured as a flat oval having opposite straight parallel walls along a longer axis of said flat oval cross-sections, said walls merge into another via semi-circular curves along a shorter axis of said flat oval, said longer axis of said cross-section extending in a plane of a curve of said curved hollow needle, and
   a surgical thread having a stiffened end inserted into said curved hollow needle, said stiffened end having a circular cross section,
   a length dimension of said longer axis and a radius of curvature of said curved hollow needle being adapted to a length dimension of said stiffened end or accordingly vice versa in that the stiffened end of the surgical thread able to be pushed through said curved hollow needle easily without skewing or twisting or deviating from said plane, and wherein said shorter axis of said cross-section of said curved hollow needle corresponds approximately to a diameter of said circular cross-section of said stiffened end of said thread to be pushed through said curved hollow needle.

2. The needle attachment assembly of claim 1, wherein the length ratio of the longer axis to the shorter axis of the curved hollow needle is 3:1.

3. The needle attachment assembly of claim 1, wherein the surgical thread is a multifilament thread having its distal ends combined together by a sleeve.

4. A surgical sewing instrument comprising:
   an approximately rod-like body having a proximal end and a distal end;
   a surgical thread having a stiffened end section that is guided from the proximal end to the distal end of the rod-like body, said stiffened end section having a circular cross section; and
   a needle attachment, the needle attachment comprising:
      a hollow shaft-like body,
      a connector on a proximal end of said hollow shaft-like body for connecting the needle attachment to a surgical instrument, and
      a curved hollow needle at a distal end of said hollow shaft-like body, the curved hollow needle having a cross-section configured as a flat oval having opposite straight parallel walls along a longer axis of said flat oval cross-sections said walls merge into another via semi-circular curves along a shorter axis of said flat oval, said longer axis of said cross-section extending in a plane of a curve of said curved hollow needle,
      wherein a length dimension of said longer axis and a radius of curvature of said curved hollow needle being adapted to a length dimension of said stiffened end or accordingly vice versa,
      wherein the stiffened end of the surgical thread is pushed through said curved hollow needle easily without skewing or twisting or deviating from said plane, and
      wherein said shorter axis of said cross-section of said curved hollow needle corresponds approximately to a diameter of said circular cross-section of said stiffened end of said thread to be pushed through said curved hollow needle.

5. The surgical sewing instrument of claim 4, wherein the approximately rod-like body has a region of recess.

6. The surgical sewing instrument of claim 5, wherein a section of the thread is exposed in the region of recess.

7. The surgical sewing instrument of claim 4, wherein the thread is a single thread or composed bundle of threads.

8. The surgical sewing instrument of claim 4, further comprising a connector on the distal end of the approximately rod-like body, the connector on the distal end of the approximately rod-like body protrudes distally and is attached to the connector on a proximal end of said hollow shaft-like body for connecting the needle attachment to a surgical instrument.

9. The surgical sewing instrument of claim 4, wherein the connector includes a hollow journal, the thread passing through hollow journal into the hollow shaft-like body of the needle attachment.

10. A needle attachment assembly for a surgical instrument, comprising:
   a hollow shaft-like body,
   a connector on a proximal end of said hollow shaft-like body for connecting the needle attachment to a surgical instrument,
   a curved hollow needle at a distal end of said hollow shaft-like body the curved hollow needle having a cross-section configured as a flat oval having opposite straight parallel walls along an entirety of a longer axis of said flat oval cross-sections said walls directly merging into another via semi-circular curves along a shorter axis of said flat oval, said longer axis of said cross-section extending in a plane of a curve of said curved hollow needle, and
   a surgical thread having a stiffened end, the stiffened end of the surgical thread pushed through said curved hollow needle easily without skewing or twisting or deviating from said plane, said stiffened end having a circular cross-section,
   wherein said shorter axis of said cross-section of said curved hollow needle corresponds approximately to a diameter of said circular cross-section of said stiffened end of said thread to be pushed through said curved hollow needle.

11. The needle attachment assembly of claim 10, wherein the stiffened end is guided laterally so that no wedging can occur when the curved hollow needle is traversed by the stiffened end.

* * * * *